(12) United States Patent
Byrne

(10) Patent No.: US 9,808,315 B2
(45) Date of Patent: Nov. 7, 2017

(54) ANCHORING FOR NON-RETAINABLE FOREIGN OBJECTS

(71) Applicant: RUSH UNIVERSITY MEDICAL CENTER, Chicago, IL (US)

(72) Inventor: Richard W. Byrne, Chicago, IL (US)

(73) Assignee: Rush University Medical Center, Chicago, IL (US)

( * ) Notice: Subject to any disclaimer, the term of this patent is extended or adjusted under 35 U.S.C. 154(b) by 619 days.

(21) Appl. No.: 14/038,535

(22) Filed: Sep. 26, 2013

(65) Prior Publication Data

US 2014/0107626 A1 Apr. 17, 2014

Related U.S. Application Data

(60) Provisional application No. 61/712,640, filed on Oct. 11, 2012.

(51) Int. Cl.
*A61B 19/02* (2006.01)
*A61B 50/20* (2016.01)
(Continued)

(52) U.S. Cl.
CPC .......... *A61B 19/0256* (2013.01); *A61B 50/20* (2016.02); *A61B 50/30* (2016.02);
(Continued)

(58) Field of Classification Search
CPC ...................................... A45F 5/004
(Continued)

(56) References Cited

U.S. PATENT DOCUMENTS 3,630,202 A 12/1971 Small
3,736,935 A * 6/1973 Reimels ............... A61F 13/2082
604/362
(Continued)

OTHER PUBLICATIONS

Rubber band explained, http://everything.explained.today/Rubber_band/, accessed Mar. 16, 2016.*
(Continued)

*Primary Examiner* — Lynsey Eiseman
*Assistant Examiner* — Dacheng Xie
(74) *Attorney, Agent, or Firm* — Barnes & Thornburg LLP; Alice O. Martin

(57) ABSTRACT

A kit and/or method for use during surgery is configured to decrease the risk of accidental retention of foreign objects, such as surgical items or medical devices, used in surgery inside of a patient after the surgery is completed. Specifically, illustrative kits may include, but not be limited to, a combination of one or more foreign objects, an anchoring member attached to a point outside of the patient or surgical field, and at least one or more connection members connecting the foreign objects to the anchoring member. Illustrative methods may include, but not be limited to, anchoring one or more foreign object by one or more connection members, wherein a first end of each connection member is attached to the foreign object, and a second end of each connection member is attached to a junction member; attaching the junction member to an anchoring member; and attaching the anchoring member to a structure that is outside the patient or surgical field.

10 Claims, 4 Drawing Sheets

(51) Int. Cl.
*A61B 50/30* (2016.01)
*A61B 17/50* (2006.01)
*A61B 90/00* (2016.01)

(52) U.S. Cl.
CPC ....... *A61B 17/50* (2013.01); *A61B 2090/0804* (2016.02); *A61B 2090/0805* (2016.02)

(58) Field of Classification Search
USPC .......................................................... 606/1
See application file for complete search history.

(56) References Cited

U.S. PATENT DOCUMENTS

| | | | | |
|---|---|---|---|---|
| 3,749,094 | A * | 7/1973 | Duncan | A61F 13/2051 |
| | | | | 604/15 |
| 5,033,462 | A * | 7/1991 | Storey, Jr. | A61F 13/00021 |
| | | | | 433/136 |
| 5,035,391 | A * | 7/1991 | Steele | A63H 27/10 |
| | | | | 248/346.03 |
| 5,074,840 | A | 12/1991 | Yoon | |
| 5,112,325 | A * | 5/1992 | Zachry | A61F 13/44 |
| | | | | 604/362 |
| 5,203,767 | A * | 4/1993 | Cloyd | A61F 13/44 |
| | | | | 604/11 |
| 5,370,656 | A | 12/1994 | Shevel | |
| 8,939,953 | B2 * | 1/2015 | Shao | A61F 13/00008 |
| | | | | 602/58 |
| 9,089,366 | B2 * | 7/2015 | Garner-Richards | A61B 19/44 |
| 2004/0188557 | A1 * | 9/2004 | Raia | G09F 21/02 |
| | | | | 242/379 |
| 2005/0049564 | A1 * | 3/2005 | Fabian | A61F 13/36 |
| | | | | 604/362 |
| 2007/0118074 | A1 * | 5/2007 | Dario | A61B 17/221 |
| | | | | 604/57 |
| 2007/0233022 | A1 * | 10/2007 | Henley | A61M 1/0088 |
| | | | | 604/305 |
| 2011/0066124 | A1 | 3/2011 | Shao | |
| 2011/0077682 | A1 | 3/2011 | Gregory et al. | |

OTHER PUBLICATIONS

Search Report & Written Opinion issued in Int'l Appl. No. PCT/US2013/062033 (2013).

* cited by examiner

ANCHORING FOR NON-RETAINABLE FOREIGN OBJECTS

CROSS REFERENCE TO RELATED APPLICATIONS

This application claims priority from U.S. Ser. No. 61/712,640 filed Oct. 11, 2012, the content of which is herein incorporated by reference in its entirety

BACKGROUND

A kit and/or method for use during surgery is described herein. The kit and/or method is configured to decrease the risk of accidental retention of foreign objects, such as surgical items or medical devices, used in surgery inside of a patient after the surgery is completed. Specifically, illustrative kits and/or methods may include, but not be limited to, a combination of one or more medical devices, surgical items and/or an anchoring member.

Surgical items such as sponges or stimulation tags may be used inside of or placed on a patient where applicable during a surgical procedure. Similarly, medical devices used during surgery are also used inside of a patient during a surgical procedure. Currently, such surgical items or medical devices are not anchored or connected to a fixed point outside of the patient. These items or devices may be lost or misplaced in the surgical field due to inadvertent and undesirable movement or obscuring caused by fluids or other tissue effluents, such as smoke during laser ablation. Consequently, this may lead to the foreign objects being accidentally retained within the patient's body after surgery. The risk of a retained foreign object such as a surgical item or medical device may be eliminated by the kit and/or method disclosed herein. Specifically, the kit may include an anchoring member to connect such foreign objects to a point outside the patient's body. Further, the foreign objects may be packaged into a traceable, easy to use, standardized kit with such an anchoring member.

Safe, reliable and simple methods for using surgical items or medical devices without the risk of the foreign objects being retained inside the patient are beneficial.

SUMMARY OF THE DISCLOSURE

A kit for use during surgery that decreases the risk of foreign objects, such as surgical items or medical devices, used in surgery being retained inside the patient after surgery is disclosed. Such a kit may include:
 (a) one or more foreign objects;
 (b) at least one anchoring member; and
 (c) one or more connection members connecting the foreign objects to the anchoring member.

A method of preventing foreign objects, such as surgical items or medical devices, from remaining inside a patient after undergoing a surgical procedure is disclosed. Such a method may comprise:
 (a) anchoring each foreign object to a connection member, wherein a first end of the connection member is attached to the foreign object, and a second end of the connection member is attached to a junction member;
 (b) attaching the junction member to an anchoring member; and
 (c) attaching the anchoring member to a structure that is outside the patient's body and is stable until detached.

Figure 1:
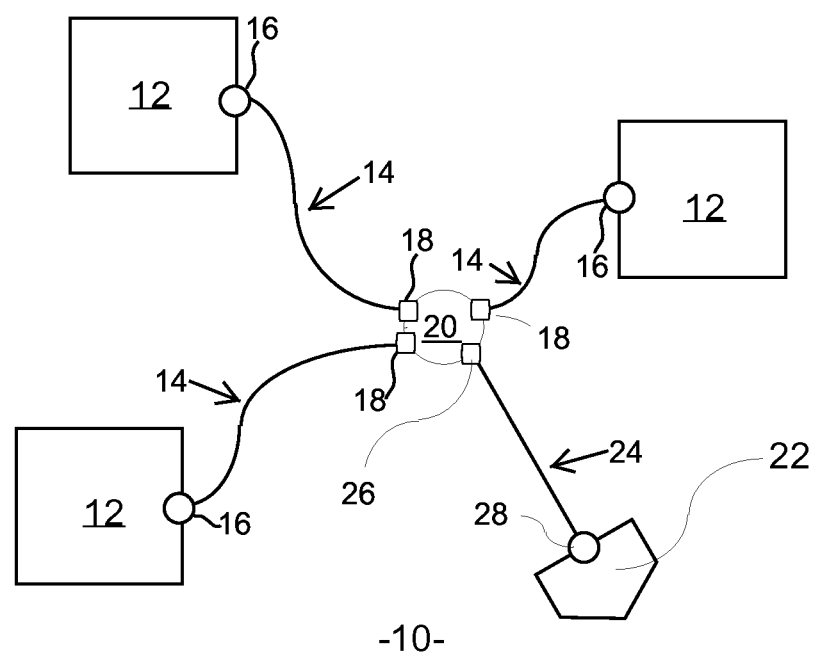
FIG. 1 shows an illustrative embodiment of a kit of the present disclosure, the kit including one or more non-retainable surgical sponges coupled together by a junction member that is further coupled to an anchoring member.

Other objects, features and advantages of the disclosed devices and methods will become apparent from the following detailed description. It should be understood the detailed description and the specific examples, while indicating preferred embodiments, are given by way of illustration only, because various changes and modifications within the spirit and scope of the invention will become apparent to those skilled in the art from the detailed description.

DETAILED DESCRIPTION

A kit for use during surgery that decreases the risk of foreign objects, such as surgical items or medical devices, used in surgery being retained inside the patient after surgery is disclosed. In illustrative embodiments, the kit includes multiple components for use during surgery, including one or more foreign objects, an anchoring member, and/or a junction member. The kit is configured to allow all of the components to be attached together to ensure that the foreign objects used inside of a patient during surgery are anchored together to a point outside of the surgical field, and therefore can be removed together after the surgery is complete to avoid unintentionally retaining any foreign objects inside the patient after surgery.

The components of the present invention may include a wide variety of items and foreign objects used during a surgical procedure. For instance, the medical devices may include, but are not limited to, sponges or tags. The surgical items may include, but are not limited to, protecting sheets, barriers, cotton balls, gauze, and surgical protectors. The anchoring members may include, but are not limited to, clips, paper fasteners, claw mechanisms, clamps, and loop-and-hook mechanisms. The junction members may include, but are not limited to, a flexible ring, tube or bar.

The foreign objects are configured to include a connection member, such as a suture, string, electronic cord or wire, to allow the components to be attached to the junction member and/or anchoring member. The connection members may be radio-opaque. Alternatively, the connection members may be made of the same material as the foreign objects or may be integrally made with the foreign objects. Alternatively, the connection members may be structurally separate or an extension of the foreign objects. In illustrative embodiments, the connection members may be attached to the foreign objects by any known means, such as surgical staples, zip ties, knots and/or soldering. The connection member may also be attached to the foreign objects by sterile glue.

In addition to coupling the foreign objects to a junction member and/or anchoring member, the connection members may also be used to couple a junction member to an anchoring member. In illustrative embodiments, the connection members are configured to provide a point of connection or attachment between the medical devices, surgical items, the anchoring members and/or junction members.

In use, the kit and its components provide an effective means of ensuring that any foreign objects, such as surgical items or medical devices, used during surgery are not inadvertently left inside a patient once the surgery is complete. The user of the kit, for example, a surgeon or surgical staff, places the kit in the area in and around the surgical field and arranges the foreign objects in appropriate locations. Appropriate locations for these foreign objects may be predetermined by the surgeon and the surgical procedures. For instance, tags may be placed in areas of the patient that should not be targeted for the surgical procedure and must be avoided. Sponges may be placed, for example, in areas where bodily fluids could obscure the surgeon's field of view and removal of the fluids is necessary. The medical devices or surgical items may be connected to the junction member, or directly to the anchoring member, either prior to or after placement of the medical devices or surgical items in the surgical field.

The anchoring member of the kit may attach to a variety of locations. For example, the anchoring member may attach to either to a surgical drape that overlays and protects the surgical field, or to some other convenient point on the patient or in the surgical area. The anchoring member may also be attached to a point on the skull or other body part of the patient. The anchoring member may also be attached to scalp hemostasis clips positioned on the patient. The anchoring member may also be attached to various objects around the surgical area, such as, but not limited to, an overhead light, bed rail, or surgical cart. The anchoring member should be attached to something outside of the patient and is preferably out of the way of the surgical work.

The junction member of the kit is configured to provide an optional central point of connection for all surgical items and medical devices. In illustrative embodiments, the surgical items and medical devices are coupled together around a single junction member, and the single junction member is then coupled directly to the anchoring member. The junction member, through a single connection member connecting the junction member to the anchoring member, permits a single connection to the anchoring member even though multiple surgical items and medical devices may be anchored by the anchoring member. In other embodiments, each surgical item and medical device may be individually coupled to the anchoring member by multiple connection members. Any number of foreign objects may be coupled to one junction member, including but not limited to a number that is complementary to certain surgical procedures, such as 3, 5 or 10 foreign objects. Moreover, multiple kits, or multiple anchoring mechanisms within one kit, may be used throughout the entire surgical area.

The process of coupling the foreign objects to the junction member, and/or the junction member to the anchoring member, may include a variety of coupling techniques. For instance, the foreign objects may be first placed in the surgical field or on the patient and then coupled to the junction member. Or the foreign objects may be manufactured as coupled to the junction member prior to surgery. Similarly, the junction member may be coupled to the anchoring member before or after the foreign objects are utilized during surgery. Other various processes are also envisioned.

The connection members of the components couple the components together and ensure that the foreign objects are ultimately linked (either directly or through the junction member) to the anchoring member outside of the patient's body. Therefore, it is important that the connection members remain intact during the entire surgical procedure. When possible, the connection members may be placed outside of the surgical field, or at least in locations that are not where the targeted surgery is being performed, when the patient is undergoing surgery. After the surgery is complete, the anchoring member may be released and the entire kit, including all foreign objects, such as medical devices or surgical items, and the anchoring member, may be removed. Prior to removal, a user such as a surgeon may perform a count of all foreign objects attached to the anchoring member to ensure all attached foreign objects used in the surgical field are not retained within the patient's body. Any combination of medical devices, surgical items and/or anchoring members may be used in a kit if necessary. Use of such kits during surgery decreases the risk of the individual attached foreign objects being lost or retained in the patient after surgery.

FIG. 1 illustrates one embodiment of a kit 10 of the present disclosure, the kit including anchored non-retainable surgical sponges 12. As illustrated, a plurality of sponges 12 (symbolized as squares) are individually attached to corresponding connection members 14 at a first end 16 of the connection members 14. A second, distal end 18 of the connection members 14 are attached to a common junction member 20. Similarly, the common junction member 20 is attached to an anchoring member 22 by a corresponding connection member 24 at a first end 26 of the connection member 26, and a second end 28 of the connection member 24 is attached to the anchoring member 22.

Figure 2:
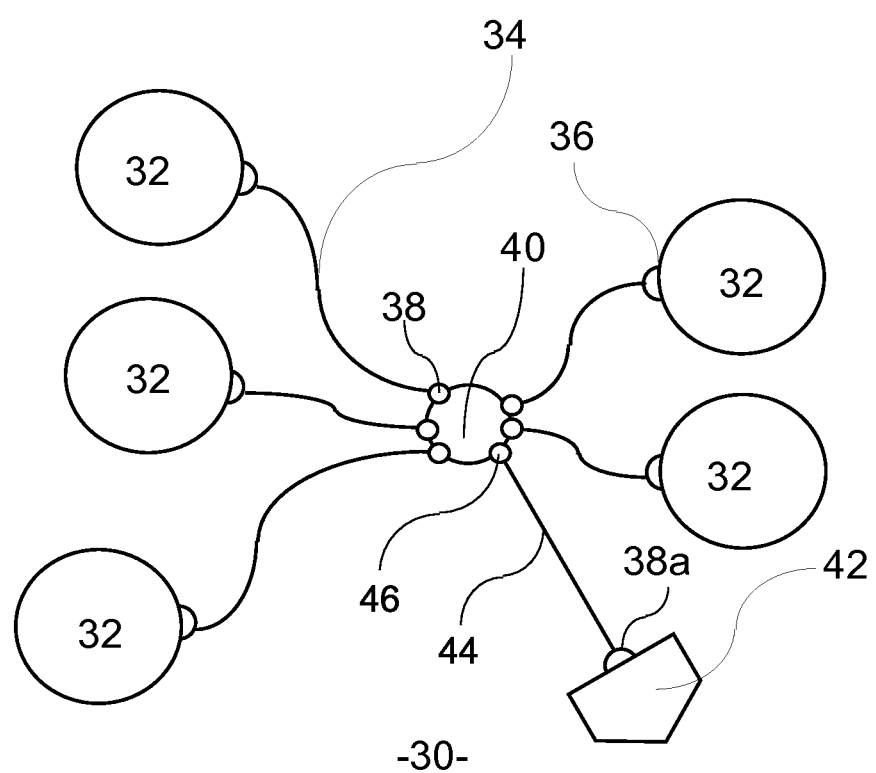
FIG. 2 shows another illustrative embodiment of a kit of the present disclosure, the kit including one or more non-retainable surgical stimulation tags anchored by a junction member that further is coupled to an anchoring member.

FIG. 2 illustrates another embodiment of a kit 30 of the present disclosure, the kit 30 including anchored non-retainable surgical tags 32. As illustrated, the plurality of tags 32 (symbolized by circles) are individually attached to corresponding connection members 34 at a first end 36 of the connection members 34. A second, distal end 38 of the connection members 34 are attached to a common junction member 40. Similarly, the common junction member 40 is attached to an anchoring member 42 by a corresponding connection member 44 at a first end 46 of the connection member 44, and a second end 38a of the connection member 44 is attached to the anchoring member 42.

Figure 3:
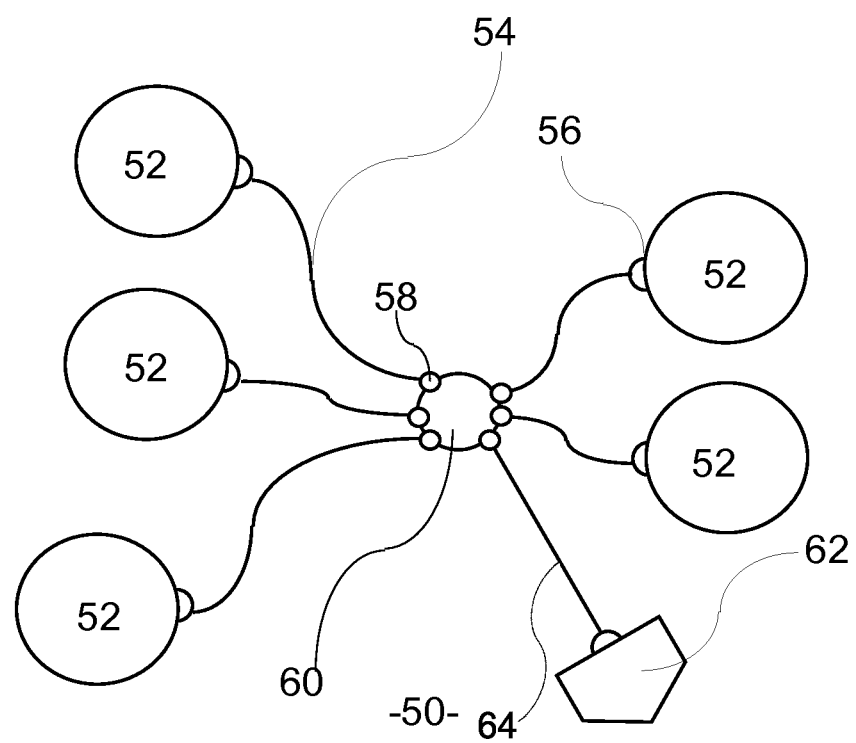
FIG. 3 shows another illustrative embodiment of a kit of the present disclosure, the kit including one or more non-retainable, non-descript foreign object anchored by a junction member that further is coupled to an anchoring member.

FIG. 3 illustrates another embodiment of a kit 50 of the present disclosure, the kit 50 including anchored non-retainable, non-descript foreign objects 52. As illustrated, a plurality of generic or non-descript foreign objects 52 (symbolized by circles) are individually attached to corresponding connection members 54 at a first end 56 of the connection members 54. A second, distal end 58 of the connection members 54 are attached to a common junction member 60. The common junction member 60 is attached to an anchoring member 62 by a separate connection member 64.

Figure 4:
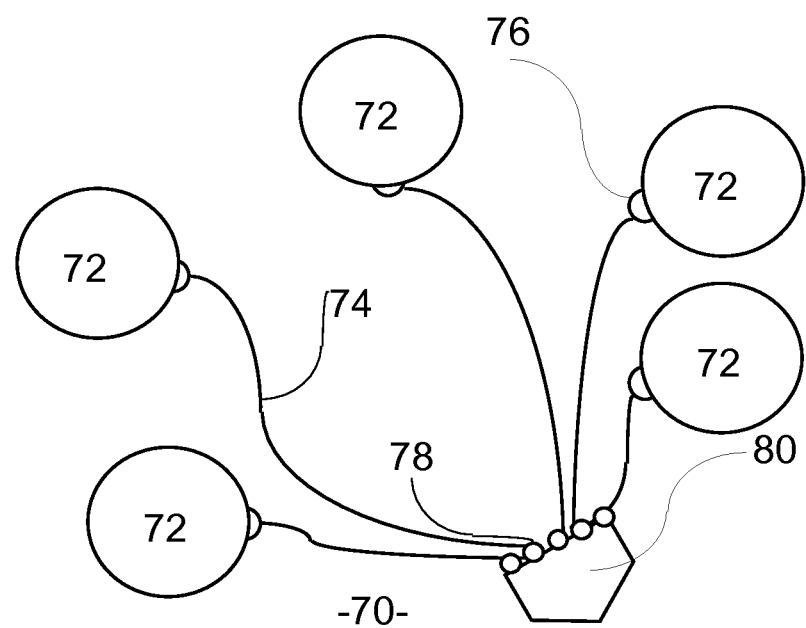
FIG. 4 shows another illustrative embodiment of a kit of the present disclosure, the kit including one or more non-retainable, non-descript foreign object anchored directly to an anchoring member.

FIG. 4 illustrates an alternate embodiment of a kit 70 of the present disclosure, the kit 70 including anchored non-retainable, non-descript foreign objects 72. As illustrated, a plurality of generic or non-descript foreign objects 72 (symbolized by circles) are individually attached to corresponding connection members 74 at a first end 76 of connection members 74. A second, distal end 78 of connection members 74 are directly connected to an anchoring member 80. In this embodiment, no junction member is disclosed.

Although the instant invention describes embodiments of various kits 10, 30, 50 and 70, as illustrated in FIGS. 1-4, it is contemplated that the instant invention can be used to retain other types of surgical items or devices. Thus, the instant disclosure should not be read to limit the use of the instant invention to sponges, tags, other medical devices, or other surgical items s for use during surgery. Furthermore, the organization and type of the individual components of a kit represent preferred embodiments and should not be read to limit the use of alternate configurations and types. One of ordinary skill in the art can discern, from the description of the instant invention, alternate embodiments contemplated by the inventors.

EXAMPLE

Examples presented are illustrative of the invention, and not limiting.

Example 1

Cortical stimulation mapping tags may get lost in the surgical field during surgery. A kit of the present invention for a cortical mapping unit may include, for example, five colored plastic tags or discs of 1 cm diameter. The tags may be numbered and connected to individual connection members such as small caliber, flexible, radio-opaque strings. The connection members may, in turn, be connected to an anchoring member that is configured to grasp or clip onto a surgical drape. Alternatively, the anchoring member may be configured to anchor directly to a patient's skull.

Current cortical mapping tags are made ad hoc at individual institutions, are not anchored, and may be lost in the surgical field. This may lead to a retained component, such as the mapping tags, being left inside the patient's body on accident. A kit of the present invention that conforms to modern operating room requirements of traceable implants reduces the risk of any of the components, such as cortical stimulation mapping tags, getting lost in the surgical field and left in a patient's body unintentionally. Such a kit also brings components, such as mapping tags and other foreign objects, together into a traceable, easy to use, standardized kit.

The invention claimed is:

1. A kit for use during open surgery that decreases the risk that foreign objects used in surgery will be unintentionally retained inside a subject of the surgery, the kit comprising: two or more of the foreign objects;
a junction member providing a single point of connection for the foreign objects;
an anchoring member, the anchoring member configured to be attached to a point outside of the subject of the surgery;
two or more connection members each having a proximal end and a distal end, wherein each proximal end is connected to a different one of the foreign objects and each distal end is connected to the junction member; and
at least a connection member extending between the junction member and the anchoring member;
wherein the anchoring member includes a clip, paper fastener, claw mechanism, clamp, or loop-and-hook mechanism.

2. The kit of claim 1, wherein the foreign objects are medical devices or surgical items.

3. The kit of claim 2, wherein the foreign objects are surgical tags.

4. The kit of claim 1, wherein the connection members connecting the foreign objects to the junction member are integrally formed with the foreign objects.

5. The kit of claim 4, wherein the connection members are made of the same material as the foreign objects.

6. The kit of claim 5, wherein the distal end of the connection members are spaced away from the foreign objects.

7. The kit of claim 1, wherein the junction member is configured to be located within the surgical field during surgery.

8. The kit of claim 1, wherein the junction member is made of flexible material.

9. The kit of claim 8, wherein the junction member is a ring, bar or tube.

10. The kit of claim 1, wherein each foreign object is connected to a different connection member, and wherein each connection member is connected to the junction member.

* * * * *